United States Patent [19]
James, Jr. et al.

[11] Patent Number: 4,806,233
[45] Date of Patent: Feb. 21, 1989

[54] METHOD OF SEPARATING A HOT HYDROCARBONACEOUS STREAM

[75] Inventors: Robert B. James, Jr.; Tom N. Kalnes, both of Des Plaines, Ill.

[73] Assignee: UOP Inc. Des Plaines, Ill.

[21] Appl. No.: 90,276

[22] Filed: Aug. 28, 1987

[51] Int. Cl.$^4$ .................. C10G 9/16; C07C 5/28
[52] U.S. Cl. .................. 208/262.1; 208/284; 208/263; 505/854
[58] Field of Search .............. 208/262, 263, 284, 286, 208/203, 311, 340; 423/481, 240; 585/854, 359

[56] References Cited

U.S. PATENT DOCUMENTS

| | | | |
|---|---|---|---|
| 1,784,202 | 12/1930 | Wheeler et al. | 208/284 |
| 2,976,229 | 3/1961 | Brown et al. | 208/203 X |
| 2,986,514 | 5/1961 | Akers et al. | 208/284 |
| 3,227,772 | 1/1966 | Drehman | 201/262 X |
| 3,547,806 | 12/1970 | Matyear | 208/262 X |
| 3,595,931 | 7/1971 | Hay et al. | 260/668 |
| 3,892,818 | 7/1975 | Scharfe et al. | 260/676 R |
| 3,919,398 | 11/1975 | Davis | 423/481 |
| 4,719,007 | 1/1988 | Johnson et al. | 208/202 X |

Primary Examiner—Glenn Caldarola
Attorney, Agent, or Firm—Thomas K. McBride

[57] ABSTRACT

A method of separating a hot hydrocarbonaceous stream having a temperature above the dew point of water and comprising hydrogen, vaporous hydrocarbonaceous compounds and an acidic inorganic compound which method comprises: (a) contacting the hot hydrocarbonaceous stream at a temperature above the dew point of water in a contacting zone with an aqueous alkaline solution in an amount sufficient to simultaneously neutralize the acidic inorganic compound and to cool the hot hydrocarbonaceous stream to a temperature below the dew point of water to produce a flowing stream comprising a hydrogen-rich gas, a liquid hydrocarbonaceous phase and an aqueous solution containing inorganic neutralization products; and (b) introducing the flowing stream produced in step (a) into a separation zone to gravitationally produce an aqueous phase containing inorganic neutralization products, a hydrogen-rich gaseous phase and a hydrocarbonaceous liquid phase.

22 Claims, 1 Drawing Sheet

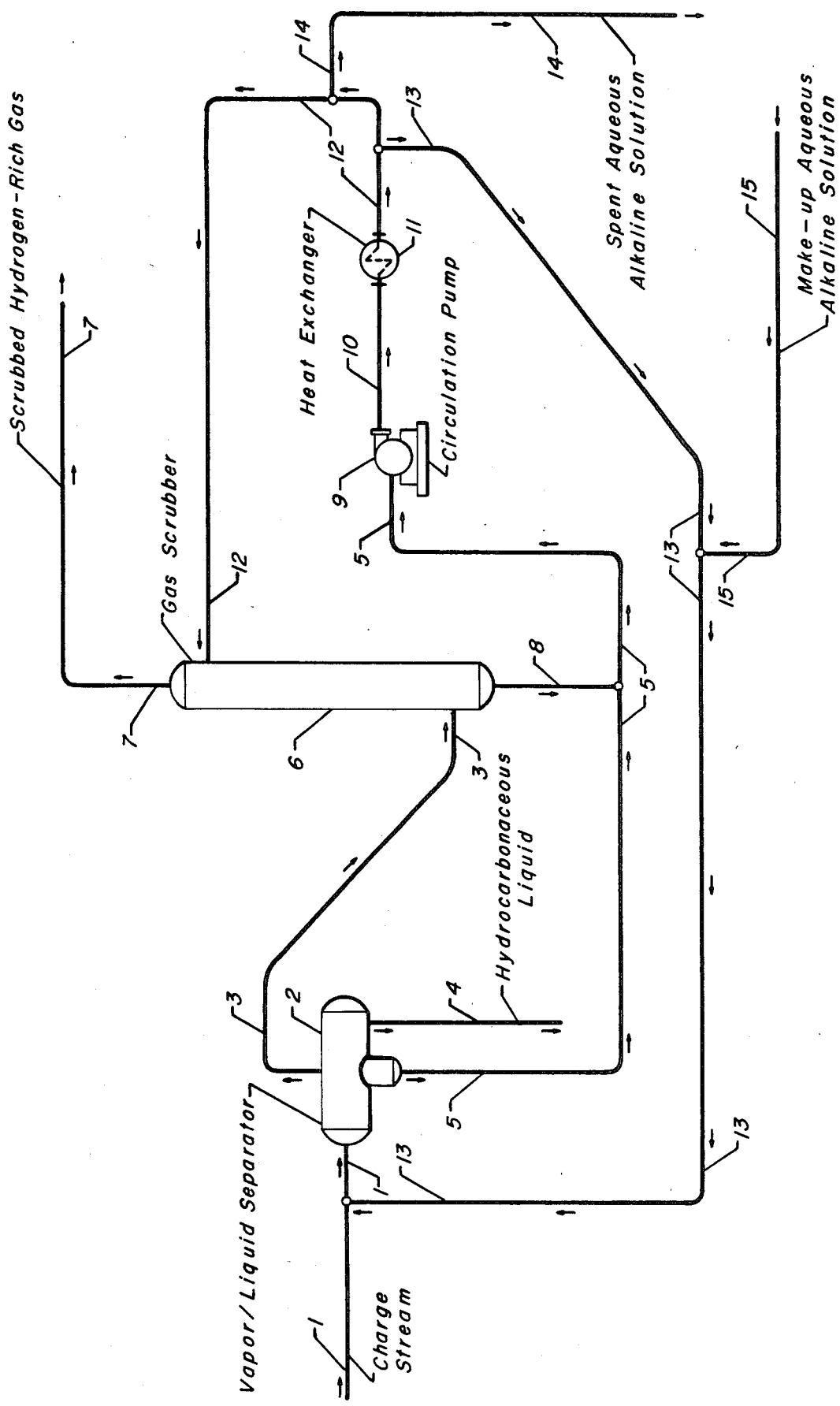

METHOD OF SEPARATING A HOT HYDROCARBONACEOUS STREAM

FIELD OF THE INVENTION

The invention relates to the broad field of separating a hot hydrocarbonaceous stream. The invention may also be broadly classified as relating to a method for separating and cooling a hot hydrocarbonaceous stream. The subject invention may be further characterized as relating to separating a hot hydrocarbonaceous stream which contains hydrogen and an acidic inorganic compound.

INFORMATION DISCLOSURE

In U.S. Pat. No. 3,919,398 (Davis), a method is disclosed for recovering bromine as hydrogen bromide from aromatic bromides. The method involves reacting the aromatic bromides with hydrogen at a temperature within the range from about 200° to about 600° C. in the presence of a palladium activated catalyst.

In U.S. Pat. No. 3,892,818 (Scharfe et al.), a method is disclosed for the conversion of hydrocarbon chlorides in the presence of hydrogen to hydrocarbons and hydrogen chloride wherein the process takes place in a gaseous phase and in the presence of a rhodium-containing catalyst.

In U.S. Pat. No. 3,595,931 (Hay et al.), a method is disclosed for the replacement of a halogen moiety in a halogenated aromatic with hydrogen wherein the halogenated aromatic is contacted in the vapor phase in the presence of hydrogen with a catalyst containing a minor amount of platinum or palladium and a minor amount of a hydrated alkali or alkaline earth metal oxide.

BRIEF SUMMARY OF THE INVENTION

The invention provides a method for separating a hot hydrocarbonaceous stream comprising hydrogen, vaporous hydrocarbonaceous compounds and an acidic inorganic compound whereby the hot hydrocarbonaceous stream is contacted with an aqueous alkaline solution at selected conditions to simultaneously neutralize the acidic inorganic compound and to cool the hot hydrocarbonaceous stream to aid in the subsequent separation thereof. The invention provides a novel method for cooling and neutralizing a hot hydrocarbonaceous stream while precluding the corrosive effects normally encountered in the processing equipment of the prior art processes. The present invention also contamplates the recovery and recycle of the aqueous alkaline solution.

One broad embodiment of the invention may be characterized as a method of separating a hot hydrocarbonaceous stream having a temperature above the dew point of water and comprising hydrogen, vaporous hydrocarbonaceous compounds and an acidic inorganic compound which method comprises: (a) contacting the hot hydrocarbonaceous stream at a temperature above the dew point of water in a contacting zone with an aqueous alkaline solution in an amount sufficient to simultaneously neutralize the acidic inorganic compound and to cool the hot hydrocarbonaceous stream to a temperature below the dew point of water to produce a flowing stream comprising a hydrogen-rich gas, a liquid hydrocarbonaceous phase and an aqueous solution containing inorganic neutralization products; and (b) introducing the flowing stream produced in step (a) into a separation zone to gravitationally produce an aqueous phase containing inorganic neutralization products, a hydrogen-rich gaseous phase and a hydrocarbonaceous liquid phase.

Another embodiment of the invention may be characterized as a method of separating a hot hydrocarbonaceous stream having a temperature above the dew point of water and comprising hydrogen, vaporous hydrocarbonaceous compounds and an acidic inorganic compound which method comprises: (a) contacting the hot hydrocarbonaceous stream at a temperature above the dew point of water in a contacting zone with a first aqueous alkaline solution in an amount sufficient to simultaneously neutralize the acidic inorganic compound and to cool the hot hydrocarbonaceous stream to a temperature below the dew point of water to produce a flowing stream comoprising a hydrogen-rich gas, a liquid hydrocarbonaceous phase and an aqueous solution containing inorganic neutralization products; (b) introducing the flowing stream produced in step (a) into a separation zone to gravitationally produce an aqueous phase containing inorganic neutralization products, a hydrogen-rich gaseous phase and a hydrocarbonaceous liquid phase; (c) contacting the hydrogen-rich gaseous phase with a second aqueous alkaline solution in the separation zone to ensure that the resulting hydrogen-rich gaseous phase is free from any acidic inorganic compound; (d) recovering and cooling the aqueous phase from step (b) to provide at least a portion of the first aqueous alkaline solution utilized in step (a).

Other embodiments of the subject invention encompass further details such as details of suitable hot hydrocarbonaceous streams, aqueous alkaline solutions, and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

The conversion of halogenated hydrocarbons by the hydrogenation thereof is a commercially valuable process and may be conducted for a variety of reasons including the destruction of hazardous chemicals, the recovery of reusable hydrocarbon from halogenated waste streams, the recovery of other halogen compounds such as hydrogen chloride and hydrogen bromide or simply to provide more highly hydrogenated hydrocarbonaceous compounds. Hydrogenation technology has become increasingly important as an economical alternative to high temperature incineration for the management of hazardous waste chemicals. Hydrogenation converts halogenated hydrocarbonaceous compounds to less toxic compounds which may then be used in an environmentally respoonsible manner. The hot reaction zone effluent from the catalyst hydrogenation of halogenated hydrocarbonaceous compounds represents a flowing stream which must be cooled and neutralized to facilitate the recovery of the components of the reaction zone effluent. If the hot effluent is cooled and the acidic inorganic compounds are permitted to form an aqueous acidic solution, severe and rapid corrosion of the metal components of a conversion plant are experienced. Such corrosion may be minimized by constructing the plant with metals which are resistant to the corrosive liquids, however, these metals are exceedingly expensive and are difficult to fabricate. Therefore, useful techniques for the cooling and neutralization of hot hydrocarbonaceous streams comprising acidic inorganic compounds which obviate severe plant corrosion have been sought by those skilled in the art.

We have discovered a method whereby hot hydrocarbonaceous streams containing acidic inorganic compounds may be simultaneously cooled and neutralized while minimizing or eliminating the use of vessels, piping and heat exchangers fabricated from expensive metallurgy. In accordance with one embodienmt of the present invention, we have discovered a method of separating a hot hydrocarbonaceous stream having a temperature above the dew point of water and comprising hydrogen, vaporous hydrocarbonaceous compounds and an acidic inorganic compound which method comprises: (a) contacting the hot hydrocarbonaceous stream at a temperature above the dew point of water in a contacting zone with an aqueous alkaline solution in an amount sufficient to simultaneously neutralize the acidic inorganic compound and to cool the hot hydrocarbonaceous stream to a temperature below the dew point of water to produce a flowing stream comprising a hydrogen-rich gas, a liquid hydrocarbonaceous phase and an aqueous solution containing inorganic neutralization products; and (b) introducing the flowing stream produced in step (a) into a separation zone to gravitationally produce an aqueous phase containing inorganic neutralization products, a hydrogen-rich gaseous phase and a hydrocarbonaceous liquid phase.

Even though the method of the present invention may be suitably utilized to separate any suitable hot hydrocarbonaceous stream comprising hydrogen, vaporous hydrocarbonaceous compounds and an acidic inorganic compound, the method is particularly suitable for the separation of a hot reaction zone effluent from the catalytic hydrogenation of halogenated hydrocarbonaceous compounds and therefore the method of the present invention will be particularly discussed and described in conjunction with a hot catalytic hydrogenation reaction zone effluent.

An additional advantage of the present invention is enjoyed in the event that the recovered hydrogen-rich gas is recycled to a catalytic hydrogenation reaction zone because the hydrogen-rich gas will be purified by the reduction or elimination of concentrations of hydrogen sulfide, hydrogen chloride, low molecular weight sulfur compounds and normally gaseous hydrocarbon compounds during the contacting with the aqueous alkaline solution.

One method of producing a hot hydrocarbonaceous stream which is to be separated in accordance with the present invention is the hydrogenation of halogenated hydrocarbons which include, for example, kepone, halogenated biphenyls, halogenated cyclodienes, halogenated alkanes, halogenated alkenes, halogenated phthalic anhydrides, and halogenated organic phosphates. The hydrocarbonaceous charge stock containing halogenated hydrocarbons is introduced into a hydrogenation zone and is contacted with a hydrogen-rich gaseous phase, preferably containing greater than about 70 volume percent hydrogen, and a hydrogenation catalyst maintained at hydrogenation conditions. The catalytic hydrogenation zone may contain a fixed, ebullated or fluidized catalyst bed. This hydrogenation reaction zone is preferably maintained under an imposed pressure from about atmospheric to about 2000 psig (13790 kPa gauge) and more preferably under a pressure from about 100 psig (689.5 kPa gauge) to about 1800 psig (12411 kPa gauge). The hydrogenation reaction is suitably conducted with a maximum catalyst bed temperature in the range of about 122° F. (50° C.) to about 850° F. (454° C.) selected to hydrogenate at least a portion of the halogenated hydrocarbon compounds contained in the charge stock and to produce an acidic inorganic compound. Further preferred operating conditions of the catalytic hydrogenation zone include liquid hourly space velocities in the range from about 0.35 $hr^{-1}$ to about 20 $hr^{-1}$ and hydrogen circulation rates from about 200 standard cubic feet per barrel (SCFB) (33.7 normal $m^3/m^3$) to about 30,000 SCFB (5056 normal $m^3/m^3$).

The preferred catalytic composite disposed within the hereinabove described hydrogenation zone can be characterized as containing a metallic component having hydrogenation activity, which component is combined with a suitable refractory inorganic oxide carrier material of either synthetic or natural origin. The precise composition and method of manufacturing the carrier material is not considered essential to the present invention. Preferred carrier materials are alumina, silica and mixtures thereof. Suitable metallic components having hydrogenation activity are those selected from the group comprising the metals of Groups VIB and VIII of the Periodic Table as set forth in the Periodic Table of the Elements, E. H. Sargent and Company, 1984. Thus, the catalytic composites may comprise one or more metallic components from the group of molybdenum, tungsten, chromium, iron, cobalt, nickel, platinum, iridium, osmium, rhodium, ruthenium, and mixtures thereof. The concentration of the catalytically active metallic component, or components, is primarily dependent upon a particular metal as well as the physical and/or chemical characteristics of the particular hydrogen feedstock. For example, the metallic components of Group VI-B are generally present in an amount within the range of from about 1 to about 20 weight percent, the iron-group metals in an amount within the range of about 0.2 to about 10 weight percent, whereas the noble metals of Group VIII are preferably present in an amount within the range of about 0.1 to about 5 weight percent, all of which are calculated as if these components existed within the catalytic composite in the elemental state. In addition, any catalyst employed commercially for hydrogenating middle distillate hydrocarbonaceous compounds to remove nitrogen and sulfur may function effectively in the hydrogenation zone of the present invention. It is further contemplated that hydrogenation catalytic composites may comprise one or more of the following components: cesium, francium, lithium, potassium, rubidium, sodium, copper, gold, silver, cadmium, mercury and zinc.

A catalytic hydrogenation zone having a hydrocarbonaceous charge stock comprising halogenated hydrocarbon compounds produces a hot hydrocarbonaceous effluent stream comprising hydrogen, vaporous hydrocarbonaceous compounds and an acidic inorganic compound. The hot hydrocarbonaceous effluent stream exits the catalytic hydrogenation zone at essentially the same temperature and pressure at which the hydrogenation zone is maintained. Although any hot hydrocarbonaceous stream may be utilized in the present invention, it is contemplated that most, if not all, such streams would have a temperature from about 250° F. (121° C.)

to about 850° F. (454° C.) and a pressure from about atmospheric to about 2000 psig (13790 kPa gauge).

In accordance with the present invention, the hot hydrocarbonaceous effluent stream comprising hydrogen, vaporous hydrocarbonaceous compounds and an acidic inorganic compound is contacted with an aqueous alkaline solution in an amount sufficient to neutralize the acidic inorganic compound and to cool the hot hydrocarbonaceous vapor stream to a temperature below the dew point of water to produce a flowing stream comprising a hydrogen-rich gas, a liquid hydrocarbonaceous phase and an aqueous solution containing inorganic neutralization products. The contact of the hot hydrocarbonaceous stream with aqueous alkaline solution may be performed in any convenient manner and is preferably conducted by co-current, in-line mixing which may be promoted by inherent turbulence, mixing orifices or any other suitable mixing means. The aqueous alkaline solution is preferably introduced in an amount sufficient to neutralize the acidic inorganic compound and to cool the hot hydrocarbonaceous vapor stream to a temperature below the dew point of water at the prevailing conditions existing in the contacting zone. The dew point of water will be principally determined by the operating pressure of the contacting zone and the effluent stream composition. The aqueous alkaline solution is preferably introduced in a ratio of aqueous alkaline solution to condensed volume of hydrocarbonaceous liquid from about 1:100 to about 100:1 and at a temperature from about 40° F. (5° C.) to about 300° F. (149° C.).

The type and volume of the aqueous alkaline solution are selected depending on the characteristics of the hot hydrocarbonaceous stream and preferably contains an alkaline compound such as calcium hydroxide, potassium hydroxide or sodium hydroxide. The aqueous alkaline solution preferably contains an alkaline compound in an amount from about 1 to about 45 weight percent. In any event, the aqueous alkaline solution must necessarily possess an alkaline concentration sufficient to neutralize the acidic inorganic compound or compounds which are contained in the hot hydrocarbonaceous stream. The volume of aqueous alkaline solution is selected on the basis to sufficiently cool the hot hydrocarbonaceous stream to the desired temperature. The temperature of the aqueous alkaline solution which is introduced into the contacting zone is preferably selected to be less than the bubble point of the aqueous alkaline solution. Since one of the subsequent goals is to produce an aqueous phase containing inorganic neutralization products, a sufficient volume of the aqueous alkaline solution is preferably provided to cool the hot hydrocarbonaceous stream to a temperature below the dew point of water.

The resulting admixture of the aqueous alkaline solution and the partially condensed hydrocarbonaceous vapor stream is introduced into a separation zone operated at separation conditions to gravitationally produce an aqueous phase containing inorganic neutralization products, a hydrogen-rich gaseous phase and a hydrocarbonaceous liquid phase. The separation zone may be maintained at any convenient and suitable separation conditions which may preferably include, for example, a temperature from about 40° F. (5° C.) to about 210° F. (99° C.) and a pressure from about atmospheric to about 2000 psig (13790 kPa gauge). A resulting aqueous phase containing inorganic neutralization products is recovered and is preferably cooled via indirect heat-exchange in order to serve as at least a portion of the aqueous alkaline solution which is recycled to contact the incoming hot hydrocarbonaceous stream as herein described in a preferred embodiment of the present invention. If at least a portion of the aqueous alkaline solution is recycled, it is preferred to withdraw a bleed stream of spent aqueous alkaline solution while simultaneously introducing fresh make-up aqueous alkaline solution. A resulting hydrogen-rich gaseous phase is recovered from the separation zone and if the hot hydrocarbonaceous charge stream is the effluent from a catalytic hydrogenation zone, the recovered hydrogen-rich gaseous phase is preferably recycled to the hydrogenation zone. The actual composition of the hydrogen-rich gaseous phase will depend upon the hydrocarbonaceous compounds present in the separation zone as well as the conditions prevailing in the separation zone. A resulting hydrocarbonaceous liquid phase is recovered, has a composition dependent upon the hot hydrocarbonaceous charge stream and contains dissolved hydrogen-rich gas which may be subsequently removed in a stripper to provide a stabilized liquid hydrocarbonaceous stream as required or desired.

In a preferred embodiment of the present invention, the resulting hydrogen-rich gaseous phase which is recovered in the separation zone is contacted with another aqueous alkaline solution to ensure that the resulting hydrogen-rich gaseous phase is free from any acidic organic compound which is particularly desirable in the case where the hydrogen-rich gaseous phase is recycled to a hydrogenation zone and must necessarily pass through piping, heat-exchangers and compressors, all of which may be easily damaged by the presence of acidic organic compounds. The contacting of the hydrogen-rich gaseous phase with an aqueous alkaline solution in the separation zone may be conducted in a portion of the separation zone utilized to perform the gravitational separation or may be conducted in a different vessel such as, for example, a gas scrubber which is closely associated with the gravitational separation vessel and both of which are broadly and collectively referred to herein as the separation zone.

In the drawing, the process of the present invention is illustrated by means of a simplified flow diagram in which such details as pumps, instrumentation, heat-exchange and heat-recovery circuits, compressors and similar hardware have been deleted as being non-essential to an understanding of the techniques involved. The use of such miscellaneous appurtenances are well within the purview of one skilled in the art.

With reference now to the drawing, a hot hydrocarbonaceous stream which contains hydrogen, vaporous hydrocarbonaceous compounds and an acidic inorganic compound is introduced into the process via conduit 1 and is contacted with a hereinafter described aqueous alkaline solution which is provided via conduit 13. This resulting mixture of the hot hydrocarbonaceous stream and the aqueous alkaline solution is introduced via conduit 1 into vapor/liquid separator 2. After a gravitational separation is conducted in vapor/liquid separator 2, an aqueous alkaline phase containing inorganic neutralization products is removed via conduit 5 and is joined by a hereinafter described aqueous alkaline phase containing inorganic neutralization products which is provided via conduit 8 and is transferred via pump 9 through discharge conduit 10 and introduced into heat-exchanger 11. The resulting cooled aqueous alkaline phase containing inorganic neutralization products is removed from heat-exchanger 11 via conduit 12. At least a portion of the cooled aqueous alkaline phase is removed from the process as a spent aqueous alkaline solution via conduit 14. At least another portion of the cooled aqueous alkaline phase containing inorganic neutralization products is removed from heat-exchanger 11 via conduits 12 and 13 and subsequently admixed with a make-up aqueous alkaline solution which is introduced via conduit 15. This resulting aqueous alkaline solution is carried via conduit 13 and is contacted with the hot hydrocarbonaceous stream as hereinabove described. At least another portion of the resulting cooled aqueous alkaline phase containing inorganic neutralization products is removed from heat-exchanger 11 via conduit 12 and introduced into gas scrubber 6. A liquid hydrocarbonaceous phase is removed from vapor/liquid separator 2 via conduit 4 and recovered. A hydrogen-rich gaseous stream is removed from vapor/liquid separator 2 via conduit 3 and introduced into gas scrubber 6 wherein it is contacted with an aqueous alkaline stream containing inorganic neutralization products which is introduced via conduit 12 as hereinabove described. A scrubbed hydrogen-rich gas is removed from gas scrubber 6 via conduit 7 and recovered. An aqueous alkaline stream containing inorganic neutralization products is removed from gas scrubber 6 via conduit 8 as hereinabove described.

The process of the present invention is further demonstrated by the following illustrative embodiment. This illustrative embodiment is however not presented to unduly limit the process of this invention, but to further illustrate the advantages of the hereinabove described embodiment. The following data were not obtained by the actual performance of the present invention, but are considered prospective and reasonably illustrative of the expected performance of the invention and have been prepared using commonly accepted engineering calculations.

ILLUSTRATIVE EMBODIMENT

This illustrative embodiment describes the method of separating and cooling a hot hydrocarbonaceous stream containing hydrogen and an acidic inorganic compound.

A hot hydrocarbonaceous stream passes from a hydrogenation reaction zone at a temperature of 500° F. (260° C.) and a pressure of 600 psig (4137 kPa gauge) containing 352,622 mass units per hour of hydrocarbon, 87,669 mass units per hour of hydrogen, 2400 mass units per hour of water vapor and 1058 mass units per hour of hydrogen chloride. The hot hydrocarbonaceous vapor stream is contacted with a circulating aqueous caustic solution containing about 15 weight percent sodium hydroxide in an amount of $2.310 \times 10^6$ mass units per hour and having a temperature of 145° F. (63° C.) before the initial contact. The resulting mixture of the hot hydrocarbonaceous stream and the aqueous caustic solution is introduced in a vapor/liquid separator at a temperature of 200° F. (93° C.) and a pressure of about 600 psig (4137 kPa gauge). An aqueous caustic solution containing inorganic neutralization products and having a temperature of about 200° F. (93° C.) is removed from the vapor/liquid separator, indirectly heat-exchanged to reduce the temperature to about 145° F. (63° C.) and circulated to contact the incoming hot hydrocarbonaceous stream as described hereinabove. A fresh make-up stream of aqueous caustic solution is continuously introduced into the circulating caustic loop in order to maintain a constant sodium hydroxide concentration and a slipstream of spent aqueous caustic solution is withdrawn to maintain a constant volume of circulating aqueous caustic solution. A liquid hydrocarbonaceous phase in an amount of 79,262 mass units per hour is removed from the vapor/liquid separator and is found to have the characteristics presented in Table 1.

TABLE 1

| ANALYSIS OF LIQUID HYDROCARBONACEOUS PHASE | |
|---|---|
| Specific Gravity @ 60° F. (15° C.) | 0.813 |
| Boiling Range, °F. (°C.) | 100(38)–650(343) |

A hydrogen-rich gaseous stream in an amount of 376,338 means units per hour is contacted in an upper portion of the vapor/liquid separator, utilized as a gas scrubber, with an aqueous caustic solution containing about 15 weight percent sodium hydroxide in an amount of $1.055 \times 10^6$ mass units per hour and having a temperature of 145° F. (63° C.) before the initial contact. The aqueous caustic solution is recovered from the gas scrubber section of the vapor/liquid separator together with the aqueous caustic solution which was used to contact the hot hydrocarbonaceous stream as described hereinabove, cooled and recycled. The resulting scrubbed hydrogen-rich gaseous stream is found to have the characteristics presented in Table 2.

TABLE 2

| ANALYSIS OF HYDROGEN-RICH GASEOUS STREAM | |
|---|---|
| Hydrogen, mole percent | 77.2 |
| Normally Gaseous Hydrocarbons, mole percent | 21.1 |
| Water Vapor, mole percent | 1.7 |

After extensive use of the equipment to separate and cool a hot hydrocarbonaceous stream containing hydrogen, vaporous hydrocarbons and an acidic inorganic compound as described hereinabove, an inspection of the equipment shows the absence of any erosion, corrosion or other deleterious impact on the metallurgy used to construct the operating plant. The metallurgy employed is the same as expected to be used in similar service but without the presence of an acidic inorganic compound.

The foregoing description, drawing and illustrative embodiment clearly illustrate the advantages encompassed by the process of the present invention and the benefits to be afforded with the use thereof.

We claim as our invention:

1. A method of separating a hot hydrocarbonaceous stream having a temperature above the dew point of water and comprising hydrogen, vaporous hydrocarbonaceous compounds and an acidic inorganic compound which method comprises:
   (a) contacting said hot hydrocarbonaceous stream at a temperature above the dew point of water in a contacting zone with an aqueous alkaline solution in an amount sufficient to simultaneously neutralize said acidic inorganic compound and to cool said hot hydrocarbonaceous stream to a temperature below the dew point of water to produce a flowing stream comprising a hydrogen-rich gas, a liquid hydrocarbonaceous phase and an aqueous solution containing inorganic neutralization products; and
   (b) introducing said flowing stream produced in step (a) into a separation zone to gravitationally produce an aqueous phase containing inorganic neutralization products, a hydrogen-rich gaseous phase and a hydrocarbonaceous liquid phase.

2. The method of claim 1 wherein said aqueous phase containing inorganic neutralization products is recovered and cooled to provide at least a portion of said aqueous alkaline solution utilized in step (a).

3. The method of claim 1 wherein said acidic inorganic compound is selected from the group consisting of hydrogen chloride, hydrogen fluoride and hydrogen bromide.

4. The method of claim 1 wherein said hydrogen-rich gaseous phase contains greater than about 70 volume percent hydrogen.

5. The method of claim 1 wherein said aqueous alkaline solution comprises an alkaline compound selected from the group consisting of sodium hydroxide, potassium hydroxide and calcium hydroxide 6. The method of claim 1 wherein said hot hydrocarbonaceous stream has a temperature from about 215° F. (102° C.) to about 1000° F. (538° C.).

7. The method of claim 1 wherein said aqueous alkaline solution is introduced into said contacting zone at a temperature less than the bubble point of said solution.

8. The method of claim 1 wherein said aqueous alkaline solution contains an alkaline compound in an amount from about 1 to about 45 weight percent.

9. The method of claim 1 wherein said aqueous alkaline solution is introduced into said contacting zone at a temperature from about 40° F. (5° C.) to about 300° F. (149° C.) and in a ratio of aqueous alkaline solution to condensed volume of hydrocarbonaceous liquid from about 1:100 to about 100:1.

10. The method of claim 1 wherein said separation zone is maintained at a temperature from about 40° F. (5° C.) to about 210° F. (99° C.) and a pressure from about atmospheric to about 2000 psig (13790 kPa gauge).

11. A method of separating a hot hydrocarbonaceous stream having a temperature above the dew point of water and comprising hydrogen, vaporous hydrocarbonaceous compounds and an acidic inorganic compound which method comprises:

(a) contacting said hot hydrocarbonaceous stream at a temperature above the dew point of water in a contacting zone with a first aqueous alkaline solution in an amount sufficient to simultaneously neutralize said acidic inorganic compound and to cool said hot hydrocarbonaceous stream to a temperature below the dew point of water to produce a flowing stream comprising a hydrogen-rich gas, a liquid hydrocarbonaceous phase and an aqueous solution containing inorganic neutralization products;

(b) introducing said flowing stream produced in step (a) into a separation zone to gravitationally produce an aqueous phase containing inorganic neutralization products, a hydrogen-rich gaseous phase and a hydrocarbonaceous liquid phase;

(c) contacting said hydrogen-rich gaseous phase with a second aqueous alkaline solution in said separation zone to ensure that the resulting hydrogen-rich gaseous phase is free from any acidic inorganic compound;

(d) recovering and cooling said aqueous phase from step (b) to provide at least a portion of said first aqueous alkaline solution utilized in step (a).

12. The method of claim 11 wherein said acidic inorganic compound is selected from the group consisting of hydrogen chloride, hydrogen fluoride and hydrogen bromide.

13. The method of claim 11 wherein said hydrogen-rich gaseous phase contains greater than about 70 volume percent hydrogen.

14. The method of claim 11 wherein said first aqueous alkaline solution comprises an alkaline compound selected from the group consisting of sodium hydroxide, potassium hydroxide and calcium hydroxide.

15. The method of claim 11 wherein said second aqueous alkaline solution comprises an alkaline compound selected from the group consisting of sodium hydroxide, potassium hydroxide and calcium hydroxide.

16. The method of claim 11 wherein said hot hydrocarbonaceous vapor stream has a temperature from about 215° F. (102° C.) to about 1000° F. (538° C.).

17. The method of claim 11 wherein said first aqueous alkaline solution is introduced into said contacting zone at a temperature less than the bubble point of said solution.

18. The method of claim 11 wherein said second aqueous alkaline solution is introduced into said contacting zone at a temperature less than the bubble point of said solution.

19. The method of claim 11 wherein said first aqueous alkaline solution contains an alkaline compound in an amount from about 1 to about 45 weight percent.

20. The method of claim 11 wherein said second aqueous alkaline solution contains an alkaline compound in an amount from about 1 to about 20 weight percent.

21. The method of claim 11 wherein said first aqueous alkaline solution is introduced into said contacting zone at a temperature from about 40° F. (5° C.) to about 300° F. (149° C.) and in a ratio of aqueous alkaline solution to condensed volume of hydrocarbonaceous liquid from about 1:100 to about 100:1.

22. The method of claim 11 wherein said separation zone is maintained at a temperature from about 40° F. (5° C.) to about 210° F. (99° C.) and a pressure from about atmospheric to about 2000 psig (13790 kPa gauge).

* * * * *